(12) United States Patent
Hongo et al.

(10) Patent No.: US 9,804,116 B2
(45) Date of Patent: Oct. 31, 2017

(54) METHOD AND DEVICE FOR DETECTING SAMPLE

(71) Applicant: Kabushiki Kaisha Toshiba, Minato-ku (JP)

(72) Inventors: Sadato Hongo, Yokohama (JP); Hirohisa Miyamoto, Kamakura (JP)

(73) Assignee: KABUSHIKI KAISHA TOSHIBA, Minato-ku (JP)

( * ) Notice: Subject to any disclaimer, the term of this patent is extended or adjusted under 35 U.S.C. 154(b) by 132 days.

(21) Appl. No.: 14/959,133

(22) Filed: Dec. 4, 2015

(65) Prior Publication Data
US 2016/0187335 A1 Jun. 30, 2016

(30) Foreign Application Priority Data

Dec. 26, 2014 (JP) .................................. 2014-263899
Nov. 11, 2015 (JP) .................................. 2015-221337

(51) Int. Cl.
*G01N 27/40* (2006.01)
*G01N 33/543* (2006.01)
*G01N 15/12* (2006.01)
*B82Y 5/00* (2011.01)
*B82Y 15/00* (2011.01)

(52) U.S. Cl.
CPC ............. *G01N 27/40* (2013.01); *G01N 15/12* (2013.01); *G01N 33/54346* (2013.01); *G01N 33/54366* (2013.01); *B82Y 5/00* (2013.01); *B82Y 15/00* (2013.01); *G01N 2015/1236* (2013.01)

(58) Field of Classification Search
CPC .. G01N 27/40; G01N 15/12; G01N 33/54346; G01N 33/54366; G01N 2015/1236; B82Y 15/00; B82Y 5/00
See application file for complete search history.

(56) References Cited

U.S. PATENT DOCUMENTS

| 4,191,739 | A | 3/1980 | Uzgiris et al. |
| 2006/0062794 | A1 | 3/2006 | Nakayama |
| 2006/0183112 | A1 | 8/2006 | Min et al. |
| 2007/0202495 | A1 | 8/2007 | Mayer et al. |
| 2007/0231926 | A1 | 10/2007 | Ikeda |

(Continued)

FOREIGN PATENT DOCUMENTS

| CA | 2250128 A1 | 10/1997 |
| CN | 1701234 A | 11/2005 |

(Continued)

*Primary Examiner* — Arun S Phasge
(74) *Attorney, Agent, or Firm* — Oblon, McClelland, Maier & Neustadt, L.L.P.

(57) ABSTRACT

According to one embodiment, a method for detecting a sample includes preparing a device for detecting a sample, the device including a measurement cassette, a first chamber formed by partitioning the cassette with a partition wall, a through-hole provided in the partition wall, a first electrode provided in the cassette, and a second electrode provided in the cassette, introducing a reagent and a sample containing a measuring object substance into the first chamber, introducing a conductive liquid into the second chamber, supplying current to the through-hole, allowing the measuring object substance whose surface is bound to and is covered by the tag particles via the capture substance in the first chamber to pass through the through-hole, and detecting presence of the measuring object substance.

13 Claims, 6 Drawing Sheets

(56) References Cited

U.S. PATENT DOCUMENTS

2009/0136958 A1 5/2009 Gershow et al.
2011/0308950 A1 12/2011 Sakai et al.
2014/0255911 A1 9/2014 Hongo et al.

FOREIGN PATENT DOCUMENTS

| | | |
|---|---|---|
| CN | 101046464 A | 10/2007 |
| CN | 202066824 U | 12/2011 |
| CN | 102507395 A | 6/2012 |
| EP | 0 923 645 A1 | 6/1999 |
| EP | 2 884 270 A1 | 6/2015 |
| JP | 2001-501806 | 2/2001 |
| JP | 2011-501806 | 1/2011 |
| JP | 2014-35229 | 2/2014 |
| JP | 2014-173936 | 9/2014 |
| WO | WO 97/35981 | 10/1997 |
| WO | WO 98/20351 A1 | 5/1998 |

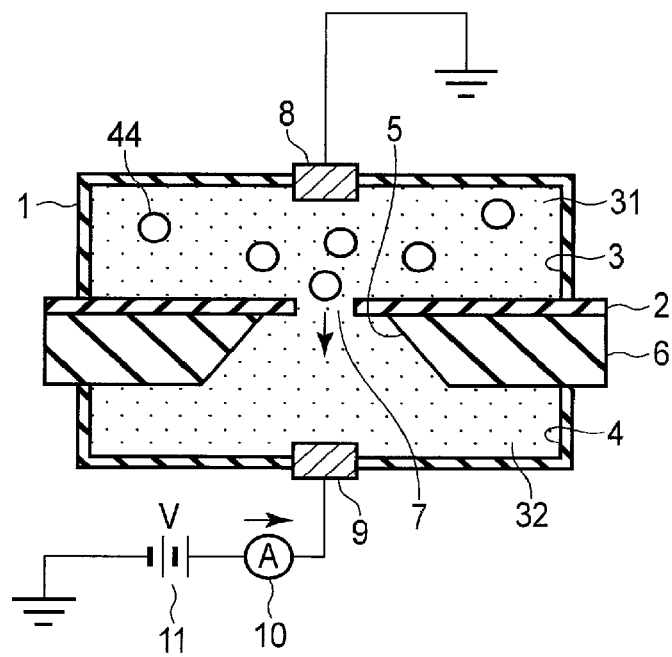
F I G. 1
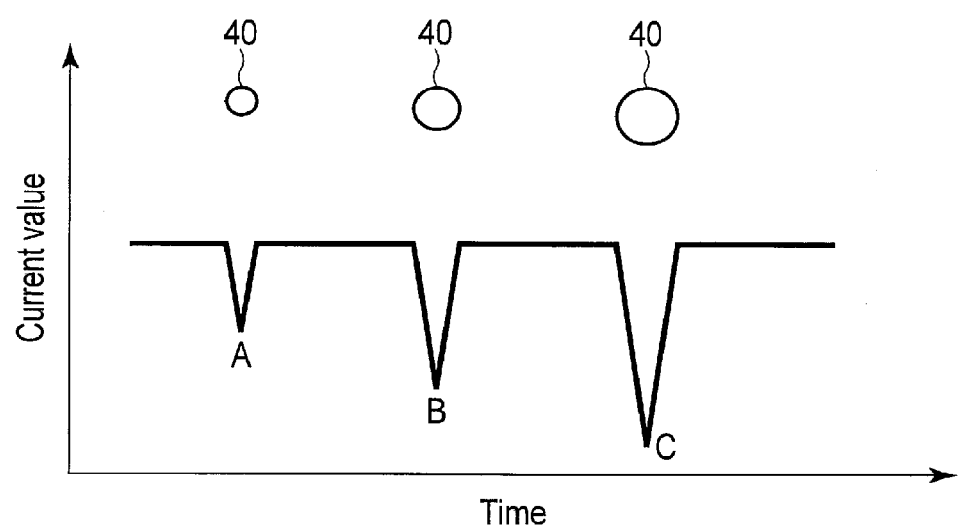
F I G. 2

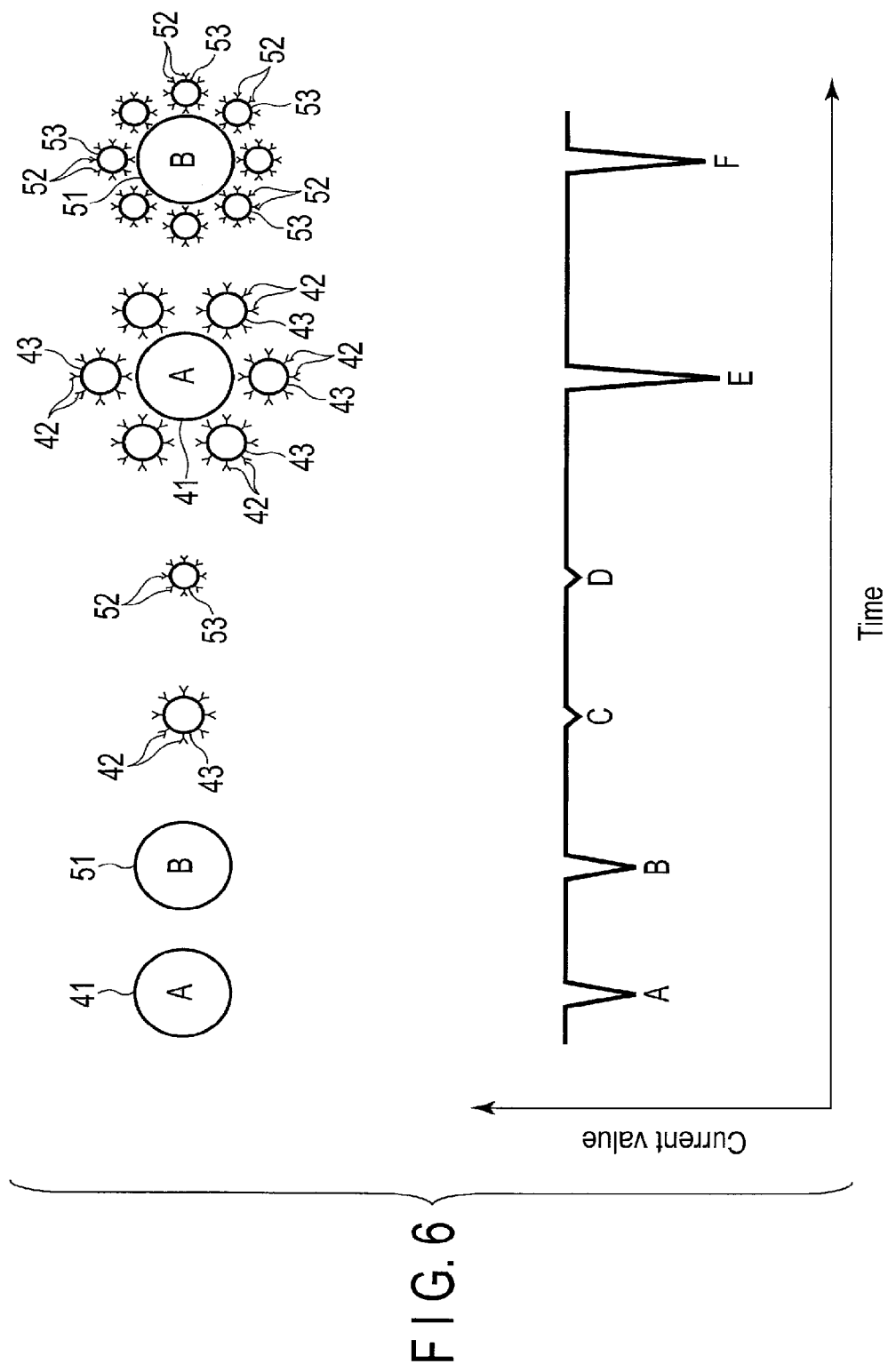
F I G. 6

METHOD AND DEVICE FOR DETECTING SAMPLE

CROSS-REFERENCE TO RELATED APPLICATIONS

This application is based upon and claims the benefit of priority from Japanese Patent Applications No. 2014-263899, filed Dec. 26, 2014; and No. 2015-221337, filed Nov. 11, 2015, the entire contents of all of which are incorporated herein by reference.

FIELD

Embodiments described herein relate generally to a method and a device for detecting a sample used to detect, for example, the virus or bacterium in the sample.

BACKGROUND

Recently, infectious diseases caused by viruses, such as Ebola hemorrhagic fever and dengue fever, have been rapidly widespread in the world and grown into social issues. To prevent a pandemic, for example, appropriate isolation of a patient after the onset of symptoms is very important. Furthermore, a patient who is infected but free of symptoms needs to be properly determined to prevent the diffusion of the virus because of the patient. This prevention will be also important in the future.

The existing detection method using immunochromatography is an effective method since results can be obtained relatively in a short time at very low cost. However, the detection sensitivity is insufficient in this method even if an antibody against a virus which is the substance to be measured has been developed. In addition, the target substance cannot be detected in a state where the amount of virus is small before the onset of symptoms.

If a genetic test is conducted, at least the problem in which the target substance is not detected due to the lack of detection sensitivity can be solved. However, in a genetic test, the detection device and the reagent are expensive, and further, the inspection takes a long time.

To solve this problem, a method for identifying a virus using a nanopore is known. This method employs marker particles whose periphery is modified by an antibody specifically identifying and bound with a virus. Each marker particles is larger than each virus. Even in the early phase of infection in which the amount of virus is small, the marker particles are bound with a virus in the order of a marker particle, a virus and a marker particle. In this manner, a composite particle is formed. If the waveform of the ion current is observed when the composite particle passes through a nanopore, the waveform of the current drop signal indicates a double-peaked shape. Thus, a virus can be specifically identified. As a result, viruses can be detected one by one. The detection can be performed with high sensitivity.

However, the composite particle needs to pass through the nanopore in the order of a marker particle, a virus and a marker particle to be to be capable of observing the double-peaked waveform. Thus, the passage attitude of composite particles is restricted.

BRIEF DESCRIPTION OF THE DRAWINGS

FIG. 1 shows the general structure of a device for detecting a sample used for a method for detecting a sample according to a first embodiment.

FIG. 2 shows that the current signal differs depending on the particle dimension.

FIG. 6 shows the current signal detected in the second embodiment.

DETAILED DESCRIPTION

Figure 3A:
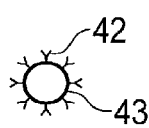
FIG. 3A and FIG. 3B show an example of a reagent used for the first embodiment.

In general, according to one embodiment, a method for detecting a sample comprises:
  preparing a device for detecting a sample, the device comprising:
    a measurement cassette;
    a first chamber and a second chamber formed by partitioning the measurement cassette with a partition wall;
    a through-hole which is provided in the partition wall and with which the first chamber and the second chamber are connected each other;
    a first electrode provided in the measurement cassette located on a first chamber side, at least a part of the first electrode being located inside the first chamber; and
    a second electrode provided in the measurement cassette located on a second chamber side, at least a part of the second electrode being located inside the second chamber;
  introducing a reagent and the sample into the first chamber, the sample containing the measuring object substance, and the reagent comprising a plurality of tag particles each having a dimension less than a dimension of the measuring object substance in the sample, and a capture substance which is bound to a surface of each of the tag particles and is specifically bound with the measuring object substance;
  introducing a conductive liquid into the second chamber;
  applying voltage between the first electrode and the second electrode;
  flowing the measuring object substance from the first chamber to the second chamber through the through-hole, a surface of the measuring object substance being bound with the plurality of tag particles via the capture substance; and
  observing change in a current flowing between the first and second electrodes to detect presence of the measuring object substance in the sample.

In general, according to an another embodiment, a device for detecting a sample, the device comprising:
  a main body;
  first and second chambers which are formed by partitioning the main body with a partition wall, the first chamber having a flow channel;

a through-hole which is provided in the partition wall and with which the flow channel in the first chamber and the second chamber are connected each other;

a sample inlet which is provided in a main body portion located on an end side of the flow channel;

an outlet which is provided in a main body portion located on the other end side of the flow channel;

a first filter provided in the flow channel, wherein the first filter is located on a downstream side of flow of a sample from the sample inlet to the outlet relative to the through-hole, and retaining a reagent comprising a plurality of tag particles each having a dimension less than a dimension of the measuring object substance in the sample, and a capture substance which is bound to a surface of each of the tag particles and is specifically bound to a surface of the measuring object substance;

a first electrode provided in a main body portion located on a first chamber side, at least a part of the first electrode being located inside the first chamber;

a second electrode provided in a main body portion located on a second chamber side, at least a part of the second electrode being located inside the second chamber; and a desorption part which desorbs the measuring object substance from the first filter to the flow channel on an upstream side of the flow of the sample, when the measuring object substance in the sample is bound with the plurality of tag particles via the capture substance in the first filter.

Various embodiments of a method for detecting a sample are explained below with reference to the device for detecting a sample shown in FIG. 1.

First Embodiment

Structure of Device for Detecting Sample

FIG. 1 is a cross-sectional view showing the general structure of a device for detecting a sample used for a method for detecting a sample according to a first embodiment.

The device for detecting a sample comprises a measurement cassette 1 which can be filled with liquid. The measurement cassette 1 is partitioned up and down by an insulating partition wall 2. A first chamber 3 is formed above the partition wall 2 inside the measurement cassette 1. A second chamber 4 is formed under the partition wall 2 inside the measurement cassette 1. A support plate 6 is provided on the lower surface of the partition wall 2 and supports the partition wall 2. A hole 5 in the form of a frustum penetrates the central part of the support plate 6. A micro-through-hole 7 penetrates in a portion of the partition wall 2 corresponding to the hole 5 of the support plate 6. Therefore, the first and second chambers 3 and 4 connect each other with the micro-through-hole 7. The diameter of the micro-through-hole 7 is sufficiently small in comparison with that of the hole 5 of the support plate 6.

For example, a first electrode 8 is provided in the upper wall portion of the measurement cassette 1 located on a first chamber 3 such that at least a part of the first electrode 8 is situated inside the first chamber 3. The first electrode 8 is arranged above the through-hole 7 of the partition wall 2. For example, a second electrode 9 is provided in the lower wall portion of the measurement cassette 1 located on a second chamber 4 such that at least a part of the second electrode 9 is situated inside the second chamber 4. The second electrode 9 is arranged under the through-hole 7 in the partition wall 2. The first electrode 8 is connected to ground. A measurement circuit 10 and a power source 11 are connected to the second electrode 9 in this order.

The measurement cassette 1 may be formed of a material which is electrically and chemically inactive as a whole. Alternatively, the measurement cassette 1 may be formed such that the inside of the first chamber 3, the inside of the second chamber 4, the contact portion with the first electrode 8 and the contact portion with the second electrode 9 are formed of a material which is electrically and chemically inactive. The measurement cassette is made of resin such as PEEK, Polycarbonate, acrylic resin, glass, sapphire, ceramic, rubber, elastomer, or etc.

The partition wall 2 may be formed of an insulating material, which is electrically and chemically inactive, such as glass, sapphire, ceramic, resin, rubber, elastomer, $SiO_2$, $Si_3N_4$ or $Al_2O_3$.

The dimension (for example, the diameter) of an opening in the through-hole 7 in the partition wall 2 is preferably not greater than 10 times of the dimension of the measuring object substance whose surface is bound to and covered by a plurality of tag particles via a capture substance as described later. The length of the through-hole 7 (equivalent to the thickness of the partition wall) is preferably equal to or slightly greater than the dimension (for example, the diameter) of the measuring object substance whose surface is covered by a plurality of tag particles.

Method for Detecting Sample Alone and Detection Signal

Hereinafter, this specification explains a method for measuring the size and the shape of the measuring object measuring object substance in a sample using the device for detecting a sample shown in FIG. 1.

First, the second chamber 4 is filled with conductive liquid 32. At this time, the second electrode 9 is partially immersed in the conductive liquid filled in the second chamber 4.

Subsequently, conductive liquid 31 and a sample containing the measuring object substance are introduced into the first chamber 3. At this time, the conductive liquid 31 in the first chamber and the conductive liquid 32 in the second chamber 4 are connected each other through the micro-through-hole 7 in the partition wall 2 and the hole 5 in the support plate 6. The first electrode 8 is partially immersed in the conductive liquid filled in the first chamber 3. At this state, current is supplied to the micro-through-hole 7 in the partition wall 2 by applying voltage between the first electrode 8 and the second electrode 9. The measuring object substance in the conductive liquid in the first chamber 3 passes through the micro-through-hole 7 and moves to the conductive liquid in the second chamber 4 because of an electric field.

FIG. 2 schematically shows the current value measured by the measurement circuit 10 when the measuring object substance passes through the micro-through-hole 7. As shown in FIG. 2, the current value changes depending on the size of the measuring object substance 40. Specifically, FIG. 2 shows that the current change peak is small as indicated by peak A when the measuring object substance 40 is small. The current change peak is larger as indicated by peaks B and C with increasing size of the measuring object substance 40. In this regard, however, when the measuring object substances 40 have the same size and different properties, it is very difficult to distinguish the measuring object substances from each other only by the change in the current value.

For conductive liquids 31 and 32 filled in the first and second chambers 3 and 4, an electrolyte solution such as an aqueous KCl solution or an aqueous NaCl solution, or a buffer solution such as a tris ethylene diamine tetra acetic acid (TB) buffer solution, a phosphate buffered saline (PBS) solution, a tris buffered saline (TBS) solution or an N-2-hydroxyetylpiperazine-N'-ethanesulphonic acid (HEPES) buffer solution can be used.

Detection Signal when Reagent is Added to Sample

Figure 3B:
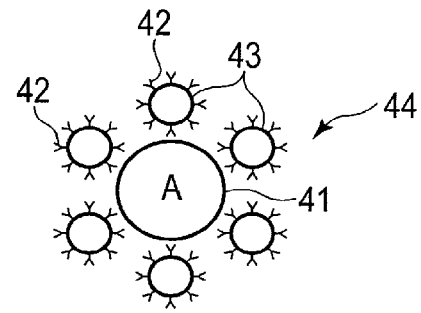

In the first embodiment, the number of types of measuring object substances (for example, biomolecules) which may be present in a sample is assumed to be one. As shown in FIG. 3A, the reagent contains a capture substance 42 and a tag particle 43. The capture substance 42 binds to a surface of the tag particle 43 and specifically binds to a surface of the measuring object substance. The tag particle 43 has a dimension (for example, a diameter) less than that of the measuring object substance. This reagent is mixed with the sample. When the measuring object substance 41 is present in the sample, as shown in FIG. 3B, a plurality of tag particles 43 are bound to and cover the surface of the measuring object substance 41 via the capture substances 42. In this manner, a composite particle 44 is obtained.

Subsequently, as shown in FIG. 1, the mixed solution 31 of the sample and the reagent is introduced into and filled in the first chamber 3. Conductive liquid 32 is filled in the second chamber 4. The sample is a conductive liquid which may contain the measuring object substance. When the sample is not a conductive liquid, or when liquid is not sufficiently supplied to the first chamber 3 with the sample alone, a mixture of the sample and the reagent may be dissolved in a conductive liquid, and this liquid may be introduced into the first chamber 3.

In this manner, the mixed solution 31 of the sample and the reagent is introduced into the first chamber 3. Subsequently, current is supplied to the micro-through-hole 7 in the partition wall 2 by applying voltage between the first electrode 8 and the second electrode 9. Particles such as the composite particle 44 in which the tag particles 43 in the first chamber 3 are bound to and cover the surface of the measuring object substance 41 via the capture substances 42 pass through the micro-through-hole 7 and move to conductive liquid 32 in the second chamber 4. At this time, the current value measured by the measurement circuit 10 changes on a pulse basis.

Figure 4:
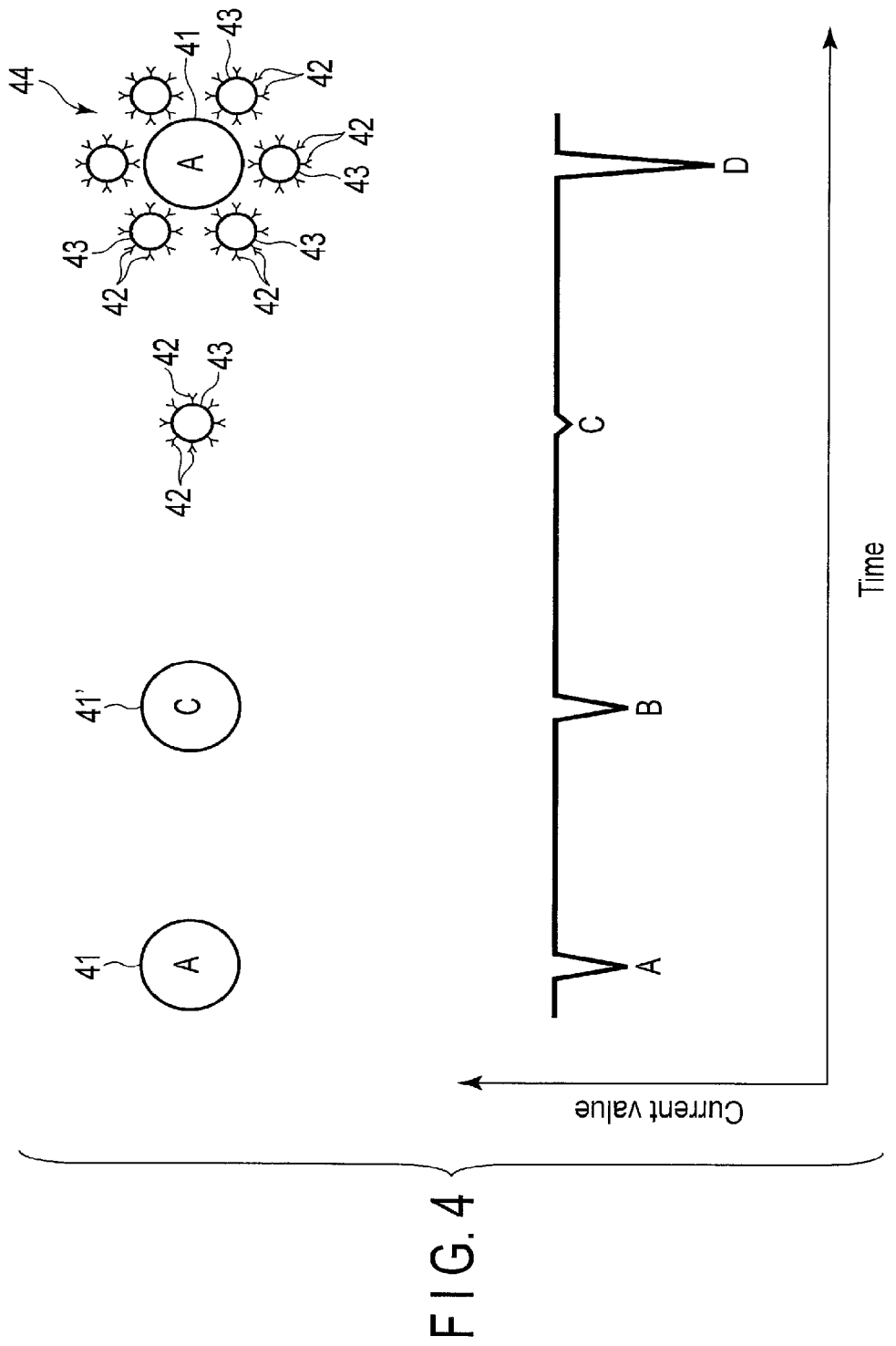
FIG. 4 shows the current signal detected in the first embodiment.

The detection signal of the current value changes depending on the dimension or the shape of the particle passing through the through-hole as shown in FIG. 4. Specifically, as shown in FIG. 4, detection signal A is obtained in a case of the measuring object substance 41 alone. Detection signal B is obtained in a case of a particle 41' alone which is different from the measuring object substance. When the dimension of the measuring object substance 41 is the same as that of the particle 41' which is different from the measuring object substance, the amount of change in the current value of the measuring object substance 41 is the same as that of the particle 41' as indicated by detection signals A and B. Thus, the measuring object substance 41 cannot be distinguished from the particle 41'. The tag particle 43 bound with the capture substances 42 emerge as detection signal C shown in FIG. 4. The amount of change in the current value of detection signal C is very small because the dimension of the tag particle 43 is set to be smaller than that of the measuring object substance 41.

Detection signal D shown in FIG. 4 is obtained in a case of the composite particle 44 in which a plurality of tag particles 43 having a dimension (for example, a diameter) less than that of the measuring object substance 41 are bound to and cover the surface of the measuring object substance 41 via the capture substances 42. The amount of change in the current value of detection signal D shown in FIG. 4 is larger than that in a case of the measuring object substance 41 alone (in other words, that of detection signal A shown in FIG. 4).

Even if the measuring object substance 41 and the particle 41' which has the same dimension as that of the measuring object substance 41 and which is different from the measuring object substance 41 are present in the sample, the measuring object substance 41 is bound with and cover with a plurality of tag particles 43 via the capture substances 42. In this manner, the measuring object substance 41 becomes larger than the different particle 41'. Thus, it is possible to determine the measuring object substance 41 alone and detect the presence of the measuring object substance 41 in the sample based on the detection signal (detection signal D) measured by the measurement circuit 10.

It is also possible to measure the concentration of the measuring object substance in the sample by monitoring the amount of change in the current value measured by the measurement circuit 10 for a certain period and counting the number of detection signals D shown in FIG. 4.

For the capture substance 42, for example, an antibody, peptide, aptamer or carbohydrate chain can be used.

The tag particle 43 is preferably spherical. For the tag particle, for example, a spherical polystyrene microparticle which is preferably negatively charged, or a nanosized gold particle can be used.

Since a tag particle binds to and covers the surface of the measuring object substance via a capture substance, the dimension (for example, the diameter) of the tag particle is less than that of the measuring object substance. When the dimension (for example, the diameter) of the measuring object substance is defined as 100%, the diameter of each tag particle is preferably greater than or equal to 10% and less than or equal to 70%; more preferably, greater than or equal to 20% and less than or equal to 50%. By setting the diameter of each tag particle so as to be greater than or equal to 10% and less than or equal to 70% of that of the measuring object substance, a plurality of tag particles bind to and cover a surface of the measuring object substance. In this manner, a structure (for example, a composite particle) whose dimension is appropriately increased can be obtained. In particular, the dimension of each tag particle is preferably selected from the lower limit side within the range of 10 to 70%. In short, a finer tag particle is preferably selected. In this manner, when a single tag particle is detected, the peak of the current value of the detection signal obtained can be maintained at a small level. As a result, it is possible to prevent the generation of noise at the time of detection.

Regarding the specific dimension relationship between the measuring object substance and each tag particles, when the dimension (for example, the diameter) of the measuring object substance is approximately 100 nm, the dimension (for example, the diameter) of each tag particle is preferably 20 to 50 nm. When the dimension (for example, the diameter) of the measuring object substance is approximately 50 nm, the dimension (for example, the diameter) of each tag particle is preferably 10 to 30 nm.

When the reagent is mixed with the sample, an amount of the tag particles in the reagent is preferably excessive in comparison with an amount of the measuring object substance in the sample. Specifically, the number of tag particles is preferably 10 to $10^6$ times that of the measuring object substances. By setting the number of tag particles in this ratio, the probability of collision and contact of tag particles with the measuring object substances is increased. Thus, tag particles can immediately bind to and cover the surface of the measuring object substance via the capture substances. As a result, it is possible to cover the surface of each measuring object substances with a plurality of tag particles before adjacent measuring object substance are bound with each other via the intervention of tag particles. Therefore, it is possible to prevent two or more measuring object substance from being bound with each other via the intervention of tag particles. In this way, for example, the formation of a dumbbell structure can be avoided. In other words, an independent microparticle in which a plurality of tag particles bind to and cover the surface of each measuring object substance can be detected by the above-described device for measuring a sample. At stated above, voltage is applied between the first and second electrodes. Then current flows through the through-hole. The change in the current value obtained by the particle passing through the through-hole is measured. In this measurement, an increase in the number of tag particles relative to the number of measuring object substance leads to an increase in the rate of emergence of the detection signal of the current value per unit time due to tag particles bound with capture substances. To lower the peak of the detection signal of the current value of tag particles and prevent the generation of noise, as described above, the dimension (diameter) of each tag particle is preferably selected from the lower limit side within the range of 10 to 70% of the dimension of the measuring object substance.

In a form in which a plurality of tag particles bind to the surface of the measuring object substance via capture substances, the tag particles preferably cover the surface of the measuring object substance such that the measuring object substance covered with the tag particles is similarity for a shape of the measuring object substance without cover of the tag particles.

Capture substances preferably bind to a tag particle such that the capture substances localize on the surface of the tag particle. In other words, it is preferred that capture substances locally bind to a surface of a tag particle. In this form, when a tag particle binds to the surface of the measuring object substance via capture substances, the tag particle shows binding anisotropy relative to the measuring object substance. For example, when a spherical, or substantially spherical tag particle is assumed, a portion corresponding to 30 to 50% of the curvature surface of the tag particle is formed by a material bound with a capture substance and a portion corresponding to the remaining curvature surface (50 to 70% of the curvature surface) of the tag particle is formed by a material which is not bound with a capture substance. Therefore, it can be manufactured the tag particle which have binding anisotropy relative to the measuring object substance.

When these types of tag particles having binding anisotropy bind to and cover the surface of the measuring object substance via capture substances, no capture substance binds to the surface (equivalent to 50 to 70% of the whole surface) excluding the surface on which tag particles bind to the measuring object substance. As a result, a tag particle exclusively binds one measuring object substance via capture substances. In this manner, the formation of a dumbbell structure can be avoided. In other words, independent composite particles in which a plurality of tag particles bind to and cover the surface of each of measuring object substances are obtained. Therefore, the above-described device for measuring a sample is capable of detecting each of the independent composite particles.

According to the first embodiment, as explained above, a sample containing the measuring object substance is introduced into the first chamber together with a reagent containing tag particles and capture substances bound with the surface of the tag particles and specifically bound with the measuring object substance. The dimension (for example, the diameter) of each tag particle to be used is less than that of the measuring object substance. A conductive liquid is introduced into the second chamber. At this state, current is supplied to the through-hole in the partition wall by applying voltage between the first electrode immersed in the mixed solution in the first chamber and the second electrode immersed in the conductive liquid in the second chamber. A specific particle passes through the micro-through-hole 7. The pulse change in the current value measured by the measurement circuit is observed. In this manner, it is possible to easily detect the presence of the measuring object substance in the sample, such as a virus or bacterium, in a short time with high sensitivity.

In sum, if the dimension (for example, the diameter) of each tag particle is greater than or equal to that of the measuring object substance, the following problems occur.
a) Because each tag particle is large, the probability of contact with the measuring object substance may be decreased, thereby increasing the required reaction time. b) In a binding state between the measuring object substance and a tag particle, for example, two measuring object substances are bound with a capture substance-tag particle-capture substance, thereby forming a composite particle having a dumbbell structure in the order of a measuring object substance, a tag particle and a measuring object substance. Thus, the detection peak has a double-peaked shape. As a result, it is necessary to identify the current waveform for detection. c) To identify the current waveform, a composite particle having a dumbbell structure needs to pass through the through-hole in the binding direction. Thus, the passage attitude is restricted. d) Since each tag particle is large, steric hindrance may occur when the tag particle binds to the measuring object substance via capture substances. Thus, the binding efficiency between the tag particle and the measuring object substance may be decreased. e) When the concentration of the measuring object substance is high in the sample, an ideal dumbbell structure cannot be obtained. Instead, the structure is shaped like a bunch of grapes. It is difficult to even detect the current waveform when the measuring object substance passes through the through-hole.

If a tag particle having a dimension (for example, a diameter) less than that of the measuring object substance is used as shown in the first embodiment, the following benefits can be obtained.

1) A tag particle having a dimension (for example, a diameter) less than that of the measuring object substance is active in Brownian movement in the solution in comparison with a tag particle having a dimension greater than or equal to that of the measuring object substance. As a result, the probability of collision and contact of tag particles with the measuring object substance is increased. Thus, the binding efficiency between the tag particle and the measuring object substance can be enhanced.

2) When a tag particle binds to the measuring object substance via capture substances, steric hindrance becomes small. Therefore, the binding efficiency between the tag particle and the measuring object substance can be increased.

3) Instead of the current waveform, the signal strength can be simply used for the determination in detection.

4) By binding a tag particle having a dimension less than that of the measuring object substance to the surface of the measuring object substance, geometric symmetry can be retained by the bound tag particles. Thus, the attitude is not restricted at the time of passage through the micro-through-hole. In this manner, the measuring object substance in the sample can be determined and detected by merely comparing the magnitude of current signals. Therefore, the detection efficiency can be improved.

It is possible to provide a method for detecting a sample such that the presence of the measuring object substance in the sample, such as a virus or a bacterium, can be easily detected in a short time with high sensitivity.

Second Embodiment

In a second embodiment, the number of types of measuring object substances (for example, biomolecules) which may be present in a sample is assumed to be two. To detect a sample, the aforementioned device for detecting a sample shown in FIG. 1 is used.

Figure 5A:
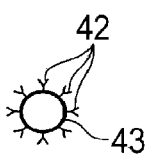
FIGS. 5A, 5B, 5C and 5D show examples of reagents used for a second embodiment.
Figure 5B:
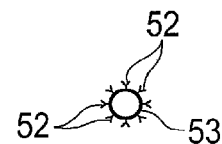
Figure 5C:
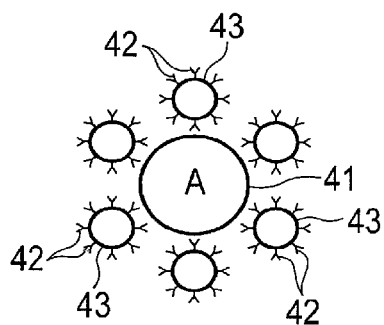
Figure 5D:
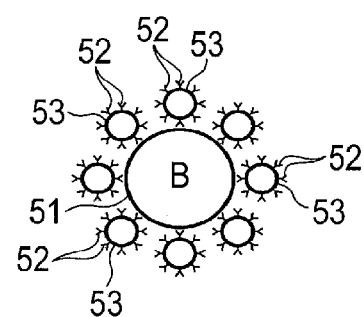

As shown in FIG. 5A, the reagent contains a first capture substance (for example, a first antibody) 42 and a first tag particle 43. The first capture substance 42 specifically binds to a surface of a first measuring object substance. The first tag particle 43 is bound with the capture substance 42 and has a dimension (diameter) less than that of the first measuring object substance. Moreover, as shown in FIG. 5B, the reagent contains a second capture substance (for example, a second antibody) 52 and a second tag particle 53. The second capture substance 52 specifically binds to a surface of a second measuring object substance. The second tag particle 53 is bound with the capture substance 52. The dimensions (for example, the diameters) of the first and second tag particles 43 and 53 are different from each other. For example, the first tag particle 43 has a diameter greater than that of the second tag particle 53. When this reagent is mixed with the sample, a plurality of first tag particles 43 bind to and cover the surface of the first measuring object substance 41 via the first capture substances 42 as shown in FIG. 5C. A plurality of second tag particles 53 bind to and cover the surface of the second measuring object substance 51 through the second capture substances 52 as shown in FIG. 5D.

Subsequently, the mixed solution of the sample and the reagent is introduced into the first chamber 3. A conductive liquid is filled in a second chamber 4. After the mixed solution of the sample and the reagent is introduced into the first chamber 3, voltage is applied between a first electrode 8 and a second electrode 9 to flow current through a micro-through-hole 7 in a partition wall 2. A first composite particle in which the first tag particles in the first chamber 3 bind to and cover the surface of the first measuring object substance 41 via the first capture substances, passes through the micro-through-hole 7 and moves to the conductive liquid in the second chamber 4. A second composite particle in which the second tag particles in the first chamber 3 bind to and cover the surface of the second measuring object substance via the second capture substances, passes through the micro-through-hole 7 and moves to the conductive liquid in the second chamber 4. When each of these composite particles passes through the micro-through-hole 7, the current value measured by a measurement circuit 10 changes on a pulse basis.

The detection signal of the current value changes depending on the dimension of the particle passing through the through-hole as shown in FIG. 6. Specifically, as shown in FIG. 6, detection signal A emerges in a case of the first measuring object substance 41 alone. Detection signal B emerges in a case of the second measuring object substance 51 alone. When the dimension of the first measuring object substance 41 is the same as that of the second measuring object substance 51, the magnitude of change in the current value of the first measuring object substance 41 is the same as that of the second measuring object substance 51 as indicated by detection signals A and B. Thus, the first and second measuring object substances 41 and 51 cannot be distinguished from each other. The first tag particle 43 bound with the first capture substances 42 and the second tag particle 53 bound with the second capture substances 52 emerge as detection signals C and D, respectively, as shown in FIG. 6. The magnitude of change in the current value of detection signals C and D is very small.

Detection signal E shown in FIG. 6 emerges in a case of the first measuring object substance 41 whose surface is bound with a plurality of first tag particles 43 having a dimension (for example, a diameter) less than that of the first measuring object substance 41 via the first capture substances 42 and is covered by the first tag particles 43; in short, in a case of the first composite particle. Detection signal F shown in FIG. 6 is obtained in a case of the second measuring object substance 51 whose surface is bound with a plurality of second tag particles 53 having a dimension (for example, a diameter) less than that of the second measuring object substance 51 via the second capture substances 52 and is covered by the second tag particles 53; in short, in a case of the second composite particle. At this time, the dimension (for example, the diameter) of the first tag particle 43 is greater than that of the second tag particle 53. Therefore, the magnitude of change in the current value at the time of passage of the first composite particle in which a plurality of first tag particles 43 bind to and cover the surface of the first measuring object substance 41 via the through-hole 7 (in short, detection signal E in FIG. 6) is larger than that of the second composite particle in which a plurality of second tag particles 53 bind to and cover the surface of the second measuring object substance 51 (in short, detection signal F in FIG. 6).

In the second embodiment, the size of the first tag particle 43 is different from that of the second tag particle 53. In this manner, the passage of the bound particle in which the first measuring object substance 41 is bound with the first tag particles 43 can be distinguished from the passage of the bound particle in which the second measuring object substance 51 is bound with the second tag particles 53.

Thus, even if the dimension of the independent first measuring object substance 41 is substantially the same as that of the independent second measuring object substance 51, and their current signals are substantially the same as each other from the detection signals measured by the measurement circuit 10, it is possible to distinguish the current signal in a state where the first measuring object substance 41 is bound with the first tag particles 43 from the current signal in a state where the second measuring object substance 51 is bound with the second tag particles 53. As a result, it is possible to determine whether the first measuring object substance 41, the second measuring object substance 51, both of them, or no measuring object substance is present in the sample.

It is also possible to measure the concentration of the first measuring object substance 41 in the sample by monitoring the amount of change in the current value measured by the measurement circuit 10 for a certain period and counting the number of detection signals E shown in FIG. 6. Similarly, it is possible to measure the concentration of the second measuring object substance 51 in the sample by counting the number of detection signals F shown in FIG. 6.

Third Embodiment

A device for detecting a sample is explained in detail with reference to FIG. 7 and FIG. 8 according to a third embodiment.

Figure 7:
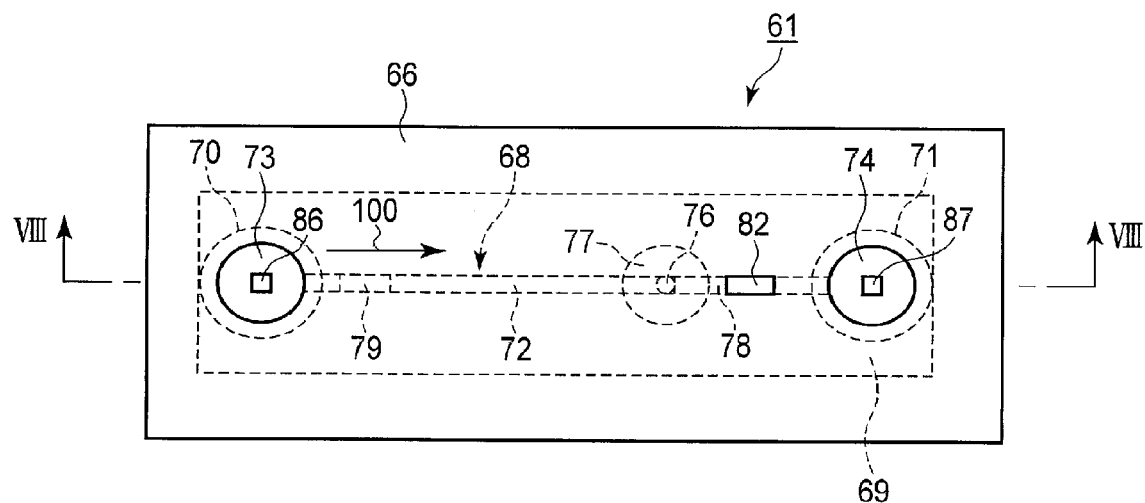
FIG. 7 is a plan view showing the general structure of a device for detecting a sample according to a third embodiment.

FIG. 7 is a plan view of the device for detecting a sample according to the third embodiment. FIG. 8 is a cross-sectional view taken along line VIII-VIII shown in FIG. 7. For example, a rectangular main body 61 comprises a rectangular block 62. An upper groove 64 and a lower groove 65 are provided with respect to a central wall 63 in the rectangular block 62. An upper cover 66 is provided on the upper surface of the block 62 so as to cover the upper groove 64. A lower cover 67 is provided on the lower surface of the block 62 so as to cover the lower groove 65.

A hollow first chamber 68 is formed in the space defined by the upper groove 64 and the upper cover 66 of the block 62 in the main body 61 having the above structure. A hollow second chamber 69 is formed in the space defined by the lower groove 65 and the lower cover 67 of the block 62.

The first chamber 68 comprises an injection port 70 located at the left end, an outflow port 71 located at the right end, and a flow channel 72 which communicates with the injection port 70 and the outflow port 71 at both ends of the flow channel 72. The flow channel 72 has narrower width than that of each of the ports 70 and 71. A sample inlet 73 is provided in the upper cover 66 above the injection port 70. A sample outlet 74 is provided in the upper cover 66 above the outflow port 71. A partition wall 75 whose planar shape is the same as that of the first chamber 68 is provided on the central wall 63 which is the bottom portion of the first chamber 68. A micro-through-hole 76 is provided in the partition wall 75 portion under the flow channel 72 on a side near the outflow port 71. A hole 77 having a diameter sufficiently greater than that of the through-hole 76 is provided in the central wall 63 facing the through-hole 76. As the through-hole 76 and the hole 77 are provided in the partition wall 75 and the central wall 63, respectively, the flow channel 72 in the first chamber 68 communicates with the second chamber 69 via the through-hole 76 and the hole 77.

A first filter 78 is provided in the flow channel 72 of the first chamber 68 on the downstream side of the flow of the sample from the sample inlet 73 to the sample outlet 74 relative to the through-hole 76. This flow of the sample is shown by the arrow 100 in FIG. 7. The first filter 78 is preferably provided in the flow channel 72 close to the through-hole 76 at a distance of 0 to 1 mm. The first filter 78 comprises, for example, a plurality of nanopillars. Each of the nanopillars is provided along the length of the flow channel 72, in other words, along the flow of the sample shown by the arrow 100. A dry reagent comprises a plurality of tag particles and capture substances bound to the surface of the tag particles and specifically bound with the measuring object substance, and is retained between the nanopillars. Each tag particles has a dimension (for example, a diameter) less than that of the measuring object substance as explained in the first embodiment.

A second filter 79 is placed in the flow channel 72 between the injection port 70 and the through-hole 76. The second filter 79 serves to absorb impurities from the sample while the sample flows in the flow channel 72 in the direction shown by the arrow 100 of FIG. 7.

A conductive-liquid inlet 80 is provided in the lower cover 67 located on the left-end side of the second chamber 69. A conductive-liquid outlet 81 is provided in the lower cover 67 located on the right-end side of the second chamber 69.

A first electrode 82 is provided in the upper cover 66 located on the first chamber 68. At least a part of the first electrode 82 is located inside the flow channel 72 adjacent to a side surface of the first filter 78 on the downstream side of the flow of the sample shown by the arrow 100. A second electrode 83 is provided in the lower cover 67 located on the second chamber 69. A part of the second electrode 83 is located inside the second chamber 69, for example, inside the second chamber 69 under the through-hole 76. A measurement circuit 84 and a DC power source 85 are connected to the second electrode 83 in this order.

A third electrode 86 is inserted into the injection port 70 of the first chamber 68 through the inlet 73 of the upper cover 66. A fourth electrode 87 is inserted into the outflow port 71 of the first chamber 68 through the outlet 74 of the upper cover 66.

The first, third and fourth electrodes 82, 86 and 87 are connected to a DC power source (not shown) through leads 88, 89 and 90, respectively, and via an on-off switch (not shown). The connection of the first, third and fourth electrodes 82, 86 and 87 to a DC power source is switched in the following processes: the process for specifically binding the measuring object substance in the sample with tag particles in the first filter 78 via capture substances and trapping the measuring object substance; the process for desorbing the measuring object substance which is specifically bound with tag particles via capture substances and is trapped in the first filter 78; and the process for allowing the measuring object substance which is specifically bound with tag particles via capture substances, and is released from the first filter 78 to the flow channel 72, to pass through the through-hole 76 and transferring the measuring object substance to the conductive liquid in the second chamber 69.

A desorption part comprises the first electrode 82, the third electrode 86 and a DC power source (not shown) configured to apply a DC voltage between these electrodes 82 and 86 while heating the first filter 78. The desorption part desorbs the measuring object substance from the first filter 78 to the flow channel 72 on an upstream side of the flow of the sample shown by the arrow 100. This measuring object substance is bound with tag particles via capture substances and is trapped in the first filter 78 as described later.

Figure 8:
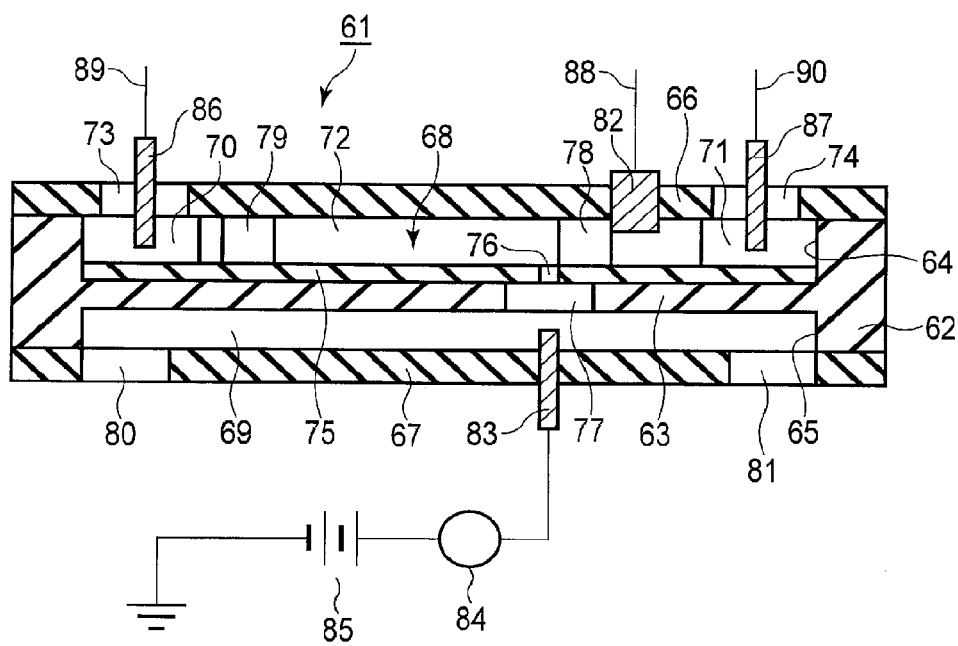
FIG. 8 is a cross-sectional view taken along line VIII-VIII of FIG. 7.

Now, a method for detecting a sample using the device for detecting a sample shown in FIG. 7 and FIG. 8 is explained according to the third embodiment. In the third embodiment, the number of types of measuring object substances (for example, biomolecules) which may be present in a sample is assumed to be one.

First, a conductive liquid is introduced into the second chamber 69 through the inlet 80 and is filled in the second chamber 69.

Subsequently, a sample is injected into the injection port 70 of the first chamber 68 through the inlet 73. The sample in the injection port 70 flows in the flow channel 72 in the direction shown by the arrow 100 of FIG. 7. The sample passes through the second filter 79 interposed in the flow channel 72. In this portion, impurities are removed. The sample further passes through the first filter 78 interposed in the flow channel 72 and flows out to the outflow port 71.

When the sample flows in the flow channel 72, a DC voltage is applied between the first and second electrodes 82 and 83. Thus, current flows through the through-hole 76 of the partition wall 75 and the hole 77 of the central wall 63. For example, the measuring object substance in the sample passes through the through-hole 76 and the hole 77 under the through-hole 76 and moves to the conductive liquid in the second chamber 69 because of an electric field. At this time, the current value measured by the measurement circuit 84 changes on a pulse basis.

The detection signal of the current value changes depending on the dimension or the shape of the particle passing through the through-hole 76 as shown in FIG. 4 explained above. Specifically, as shown in FIG. 4, detection signal A is obtained in a case of the measuring object substance 41 alone. Detection signal B is obtained in a case of a particle 41' alone which is different from the measuring object substance. When the dimension of the measuring object substance 41 is the same as that of the particle 41' which is different from the measuring object substance, the magnitude of change in the current value of the measuring object substance 41 is the same as that of the different particle 41' as indicated by detection signals A and B. Thus, the measuring object substance 41 cannot be identified from the different particle 41'. A tag particle 43 bound with capture substances 42 emerges as detection signal C shown in FIG. 4. The magnitude of change in the current value of detection signal C is very small.

The measuring object substance in the sample can be identified by the following process.

First, a conductive liquid is introduced into the second chamber 69 through the inlet 80 and is filled in the second chamber 69.

Subsequently, a sample is injected into the injection port 70 of the first chamber 68 through the inlet 73. At the same time as, or immediately after the injection, the third electrode 86 and the fourth electrode 87 are connected to a DC power source (not shown) through leads 89 and 90. The third and fourth electrodes 86 and 87 are connected to a DC power source such that the third electrode 86 is negative and the fourth electrode 87 is positive. Subsequently, a DC voltage is applied between the third and fourth electrodes 86 and 87. At this time, in general, the measuring object substance in the sample is negatively charged. Thus, the electrophoresis caused by the application of a DC voltage between the third and fourth electrodes 86 and 87 stimulates the move of the measuring object substance in the direction shown by the arrow 100 from the injection port 70 to the flow channel 72. The sample in the injection port 70 flows in the flow channel 72 because of capillarity and passes through the second filter 79 interposed in the flow channel 72. In this portion, impurities are removed. The sample further passes through the first filter 78 interposed in the flow channel 72 from the flow channel 72 and flows out to the outflow port 71. While the sample passes through the first filter 78 at appropriate speed, the first filter 78 retains a dry reagent containing tag particles and capture substances which are bound to the surface of each tag particle and are specifically bound with the measuring object substance. Thus, a plurality of composite particles in which tag particles bind to and cover the surfaces of the measuring object substance in the sample via capture substances are trapped in the first filter 78. At the same time, only the measuring object substances are trapped. Particles different from the measuring object substances pass through the first filter 78, move to the outflow port 71, flow out through the outlet 74 and are eliminated.

After plural composite particles are trapped, the first electrode 82 and the third electrode 86 are connected to a DC power source (not shown) through leads 88 and 89 such that the first electrode 82 is negative and the third electrode 86 is positive. Subsequently, a DC voltage is applied between the first and third electrodes 82 and 86. At this time, in general, the composite particles trapped in the first filter 78 are negatively charged. The first filter 78 is provided between the first and third electrodes 82 and 86. Therefore, in the first filter 78, a flow in a direction opposite to the flow of the sample shown by the arrow 100 of FIG. 7 is generated by the electrophoresis which is caused by the application of a DC voltage between the first and third electrodes 82 and 86 allows to produce. In other word, in the first filter 78, a flow for an upstream side of the flow of the sample shown by the arrow 100 is generated by the electrophoresis. By this opposite flow, when the heat is applied in the first filter 78, the composite particles trapped in the first filter 78 are desorbed and released toward the upstream side of the flow of the sample shown by the arrow 100. As a result, the composite particles are collected on the flow channel 72 near the through-hole 76 and are highly concentrated.

In the third embodiment, while the composite particles trapped in the first filter 78 are desorbed by the electrophoresis caused by the application of a DC voltage between the first and third electrodes 82 and 86, the first filter 78 may be heated to promote the desorption of the composite particles as described above.

After the composite particles are desorbed and released from the first filter 78 toward the upstream side of the flow of the sample, the connection destination of lead 88 of the first electrode 82 is switched from a DC power source (not shown) to ground. At this state, a DC voltage from the DC power source 85 is applied between the first and second electrodes 82 and 83 to supply current into the through-hole 76 in the partition wall 75. Because of the application of a DC voltage, the composite particles pass through the through-hole 76 located near the first filter 78 at a prescribed distance and the hole 77 under the through-hole 76 on the upstream side of the direction of the flow of the sample relative to the first filter 78, and move to the conductive liquid in the second chamber 69. At this time, the current value measured by the measurement circuit 84 changes on a pulse basis.

In this current detection, mainly, detection signal D shown in FIG. 4 described above is obtained in a case of a composite particle in which tag particles bind to and cover the surface of the measuring object substance via capture substances. The magnitude of change in the current value of detection signal D is larger than that in a case of the measuring object substance 41 alone, in other words, that of detection signal A shown in FIG. 4 described above.

Therefore, even if the measuring object substance and a particle which is different from the measuring object substance and has the same dimension as that of the measuring object substance are present in the sample, a composite particle in which tag particles 43 bind to and cover the surface of the measuring object substance 41 via capture substances 42 has a particle dimension greater than that of the measuring object substance 41. Thus, it is possible to determine the measuring object substance 41 alone and detect the presence of the measuring object substance 41 in the sample based on the detection signal obtained by the measurement circuit 84.

In the device for detecting a sample in the third embodiment, the first chamber 68 comprises the injection port 70, the outflow port 71 and the narrow flow channel 72 configured to connect these ports 70 and 71. The capacity of the first chamber 68 is small. Therefore, it is possible to detect the presence of the measuring object substance in a small amount of sample with high frequency.

Moreover, the first filter 78 interposed in the flow channel 72 retains the reagent in advance. The positional relationships between the first filter 78, the through-hole 76 in the partition wall 75 and the first electrode 82 are specified. Because of these structures, it is possible to form a composite particle in which tag particles effectively bind to and cover the surface of the measuring object substance in the sample via capture substances. Furthermore, it is possible to collect these composite particles in the flow channel 72 located on the upstream side of the flow of the sample relative to the first filter 78. As a result, even when the measuring object substance is present in the sample at low concentration, the presence of the measuring object substance in the sample can be detected with high frequency.

In the third embodiment, the first filter may be structured by nanowires in place of nanopillars.

The desorption part is not limited to the structure comprising the first electrode, the third electrode and a DC power source configured to apply a DC voltage between these electrodes. The desorption part may have any structure as long as it is capable of removing the measuring object substance which is trapped in the first filter 78 and whose surface is specifically bound with tag particles via capture substances (in short, a composite particle). For example, the desorption part may be configured to apply pressure to the first filter through the outlet, the outflow port and the flow channel, so that the composite particles are desorbed from the first filter.

An example of the above embodiments is explained, using the device for detecting a sample shown in FIG. 1.

Comparative Example 1

As model particles, a polystyrene microparticle which simulates the virus of the measuring object substance, is modified by biotin on the surface and has a diameter of 1 µm, and a polystyrene microparticle which is modified by streptavidin (a capture substance) on the surface, simulates a tag particle and has a diameter of 0.22 µm are prepared. The device for detecting a sample used for measurement comprises the measurement cassette 1 formed of polycarbonate. The measurement cassette 1 is partitioned up and down by the partition wall 2 made of quartz in which the through-hole 7 is provided. The first chamber 3 is provided above the partition wall 2 inside the measurement cassette 1. The second chamber 4 is provided under the partition wall 2 inside the measurement cassette 1. The through-hole 7 has a diameter of 2 µm and a length of 10 µm (equivalent to the thickness of the partition wall 2). The first electrode 8 formed of Ag/AgCl is provided in the upper wall portion of the measurement cassette 1 such that a part of the first electrode 8 is located inside the first chamber 3. The second electrode 9 formed of Ag/AgCl is provided in the lower wall portion of the measurement cassette 1 such that a part of the second electrode 9 is located inside the second chamber 4.

First, the second chamber 4 of the device for detecting a sample is filled with a PBS buffer solution which does not contain the model particles. The first chamber 3 is filled with a PBS buffer solution containing a suspended polystyrene microparticle which simulates the virus of the measuring object substance, is modified by biotin on the surface and has a diameter of 1 µm. Subsequently, bias voltage is applied between the first and second electrodes 8 and 9 made of Ag/AgCl immersed in the PBS buffer solutions in the first and second chambers 3 and 4. At this state, the current is monitored.

In this monitoring, when a bias of 100 mV is applied, a base current of 38 nA is measured. Between the time response and the current change, the following relationship is obtained: a spike-like current drop signal emerges in association with the passage of a particle through the through-hole 7.

Figure 9:
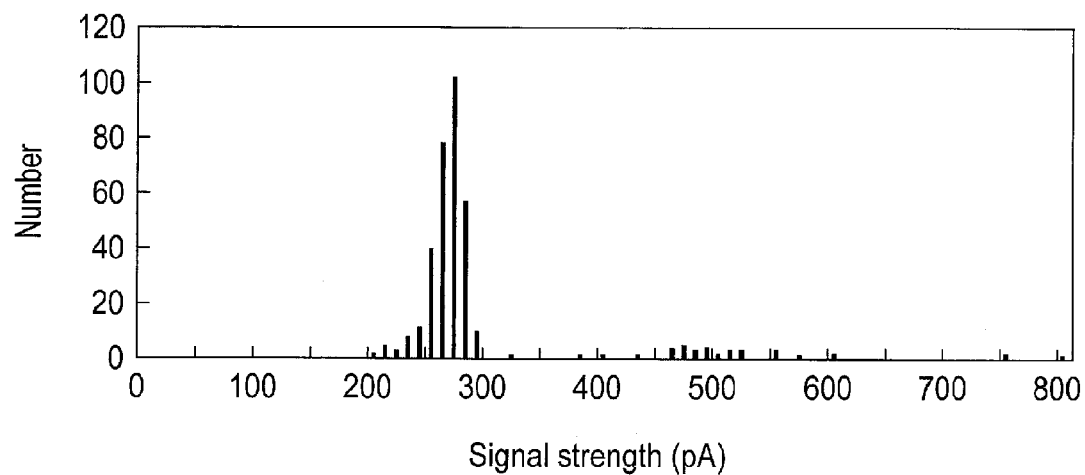
FIG. 9 shows the frequency distribution of the signal strength in reference example 1.

By regarding the amount of current drop from the base current as the signal strength based on the relationship between the time response and the current change, the frequency distribution is obtained. The results are shown in FIG. 9.

Example 1

Polystyrene microparticles each simulating the virus of the measuring object substance, being modified by biotin on the surface and having a diameter of 1 µm are mixed with polystyrene microparticles each being modified by streptavidin (a capture substance) on the surface, simulating a tag particle and having a diameter of 0.22 µm in the ratio of 1:70 in terms of the number of particles. In other words, polystyrene microparticles which simulate tag particles and have a diameter of 0.22 µm are excessively mixed with polystyrene microparticles which simulate the viruses of the measuring object substance and have a diameter of 1 µm. After the mixture, the composite is left for an hour. The second chamber 4 of the device for detecting a sample having the same structure as comparative example 1 is filled with a PBS buffer solution which does not contain the model particles. Subsequently, the first chamber 3 is filled with a PBS buffer solution containing the above suspended composite. Bias voltage is applied between the first and second electrodes 8 and 9 formed of Ag/AgCl immersed in the PBS buffer solutions in the first and second chambers 3 and 4. At this state, the current is monitored.

In this monitoring, when a bias of 100 mV is applied, a base current of 38 nA is measured. Between the time response and the current change, the following relationship is obtained: a spike-like current drop signal emerges in association with the passage of a particle through the through-hole 7.

Figure 10:
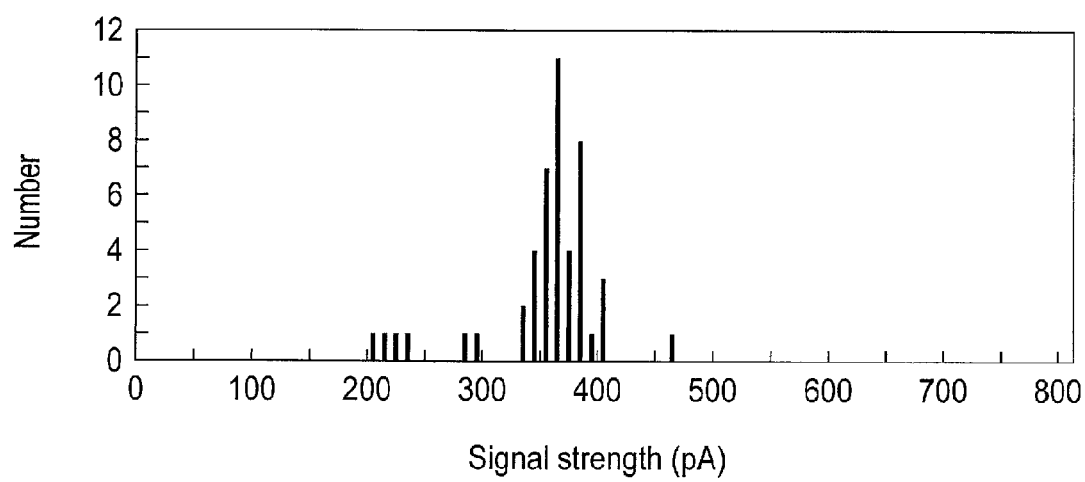
FIG. 10 shows the frequency distribution of the signal strength in example 1.

By regarding the magnitude of current drop from the base current as the signal strength based on the relationship between the time response and the current change, the frequency distribution is obtained. The results are shown in FIG. 10.

In comparative example 1 which measures only a polystyrene microparticle which simulates the virus, is modified by biotin on the surface and has a diameter of 1 µm, the peak of the signal strength is 270 pA as shown in FIG. 9. In example 1 which measures a composite particle of a polystyrene microparticle simulated the virus, is modified by biotin on the surface and has a diameter of 1 µm and a polystyrene microparticle which is modified by streptavidin (a capture substance) on the surface, simulates a tag particle and has a diameter of 0.22 µm, the peak of the signal strength is 360 pA as shown in FIG. 10. Thus, the peak of the signal strength is shifted to a large value. These results show that, in comparison with an independent polystyrene microparticle which is modified by biotin on the surface and has a diameter of 1 μm, the signal strength is increased since the dimension (for example, the diameter) is increased when a plurality of polystyrene microparticles, which are modified by streptavidin on the surface and have a diameter of 0.22 μm, bind to and cover the surface of a polystyrene microparticle which is modified by biotin on the surface and has a diameter of 1 μm.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A method for detecting a measuring object substance in a sample, the method comprising:
preparing a device for detecting a sample, the device comprising:
a measurement cassette;
a first chamber and a second chamber formed by partitioning the measurement cassette with a partition wall;
a through-hole which is provided in the partition wall and with which the first chamber and the second chamber are connected each other;
a first electrode provided in the measurement cassette located on a first chamber side, at least a part of the first electrode being located inside the first chamber; and
a second electrode provided in the measurement cassette located on a second chamber side, at least a part of the second electrode being located inside the second chamber;
introducing a reagent and the sample into the first chamber, the sample containing the measuring object substance, and the reagent comprising a plurality of tag particles each having a dimension less than a dimension of the measuring object substance in the sample, and a capture substance which is bound to a surface of each of the tag particles and is specifically bound to a surface of the measuring object substance;
introducing a conductive liquid into the second chamber;
applying voltage between the first electrode and the second electrode;
flowing the measuring object substance from the first chamber to the second chamber through the through-hole, a surface of the measuring object substance being bound with the plurality of tag particles via the capture substance; and
observing change in a current flowing between the first and second electrodes to detect presence of the measuring object substance in the sample.

2. The method of claim 1, wherein the tag particles are excessively mixed with the sample in comparison with the amount of the measuring object substance in the sample.

3. The method of claim 2, wherein the number of tag particles is 10 to $10^6$ times for the number of the measuring object substance.

4. The method of claim 1, wherein the sample and the reagent are introduced into the first chamber with a conductive liquid.

5. The method of claim 1, wherein the surface of the measuring object substance is bound with the plurality of tag particles via the capture substance, a shape of the measuring object substance covered with the tag particles being similar for a shape of the measuring object substance without a cover of the tag particles.

6. The method of claim 1, wherein the dimension of each of the tag particles is 10 to 70% of the dimension of the measuring object substance.

7. The method of claim 1, wherein the tag particles contained in the reagent include two types of tag particles having dimensions different from each other.

8. The method of claim 1, wherein the capture substance is locally bound to the surface of each of the tag particles.

9. The method of claim 1, wherein the tag particles are plastic particles or nanosized gold particles.

10. A device for detecting a sample, the device comprising:
a main body;
first and second chambers which are formed by partitioning the main body with a partition wall, the first chamber having a flow channel;
a through-hole which is provided in the partition wall and with which the flow channel in the first chamber and the second chamber are connected each other;
a sample inlet which is provided in a main body portion located on an and side of the flow channel;
an outlet which is provided in a main body portion located on the other end side of the flow channel;
a first filter provided in the flow channel, wherein the first filter is located on a downstream side of flow of a sample from the sample inlet to the outlet relative to the through-hole, and retaining a reagent comprising a plurality of tag particles each having a dimension less than a dimension of the measuring object substance in the sample, and a capture substance which is bound to a surface of each of the tag particles and is specifically bound to a surface of the measuring object substance;
a first electrode provided in a main body portion located on a first chamber side, at least a part of the first electrode being located inside the first chamber;
a second electrode provided in a main body portion located on a second chamber side, at least a part of the second electrode being located inside the second chamber; and
a desorption part which desorbs the measuring object substance from the first filter to the flow channel on an upstream side of the flow of the sample, when the measuring object substance in the sample is bound with the plurality of tag particles via the capture substance in the first filter.

11. The device of claim 10, wherein the first filter comprises a plurality of nanopillars each arranged along the flow of the sample.

12. The device of claim 10, wherein the first filter comprises a nanowire.

13. The device of claim 10, further comprising a second filter which is provided in the flow channel on the upstream side of the flow of the sample relative to the first filter and is configured to eliminate an impurity from the sample.

* * * * *